US011011268B2

(12) United States Patent
Kelkar et al.

(10) Patent No.: US 11,011,268 B2
(45) Date of Patent: May 18, 2021

(54) SYSTEM AND METHOD FOR MANAGING MEDICAL WASTE RECEIVED IN ONE OR MORE CONTAINERS

(71) Applicant: ARK TECHNOLOGIES LLC, West Sacramento, CA (US)

(72) Inventors: Mukul Kelkar, West Sacramento, CA (US); John Raatz, West Sacramento, CA (US); Victor Anderson, West Sacramento, CA (US)

(73) Assignee: ARK TECHNOLOGIES LLC, West Sacramento, CA (US)

( * ) Notice: Subject to any disclaimer, the term of this patent is extended or adjusted under 35 U.S.C. 154(b) by 215 days.

(21) Appl. No.: 16/240,553

(22) Filed: Jan. 4, 2019

(65) Prior Publication Data

US 2019/0221306 A1 Jul. 18, 2019

Related U.S. Application Data

(60) Provisional application No. 62/617,306, filed on Jan. 15, 2018.

(51) Int. Cl.
*G16H 40/20* (2018.01)
*G06Q 10/06* (2012.01)
(Continued)

(52) U.S. Cl.
CPC .......... *G16H 40/20* (2018.01); *A61B 50/362* (2016.02); *A61B 50/37* (2016.02); *B09B 3/0075* (2013.01);
(Continued)

(58) Field of Classification Search
USPC ....................................................... 705/2–3
See application file for complete search history.

(56) References Cited

U.S. PATENT DOCUMENTS 5,252,290 A * 10/1993 Uesugi ................... A61L 11/00
241/23
5,947,285 A * 9/1999 Gaba ........................ B65F 1/10
206/366

(Continued)

OTHER PUBLICATIONS

Brewer, Jeff, "A disposable choice for hospital waste", Hosp Materiel Manage Q, 1993, 14(3) 12-25, Aspen Publishers, Inc (Year: 1993).*

*Primary Examiner* — Amber A Misiaszek
(74) *Attorney, Agent, or Firm* — Maschoff Brennan

(57) ABSTRACT

A system for managing medical waste received in one or more containers placed at one or more medical facilities, for instance, for improved scheduling is disclosed. In some embodiments, the system comprises tracking modules coupled to the one or more containers, wherein each tracking module comprises, a plurality of LEDs positioned opposite to a plurality of light sensors, wherein each of the LED is being configured to periodically project a light beam towards a light sensor among plurality of light sensors for detecting a fill level of the container, and a controller in communication with the plurality of LEDs and the plurality of light sensors, wherein the controller is being configured for, periodically triggering the plurality of LEDs for projecting the light beams, receiving output data of the plurality of light sensors, the output data representing the fill level of the container, and communicating the fill level to a server.

9 Claims, 4 Drawing Sheets

(51) Int. Cl.
*B09B 3/00* (2006.01)
*A61B 50/37* (2016.01)
*A61B 50/36* (2016.01)
*B07C 5/34* (2006.01)

(52) U.S. Cl.
CPC ...... *G06Q 10/06311* (2013.01); *B07C 5/3412* (2013.01)

(56) References Cited

U.S. PATENT DOCUMENTS

| | | | | |
|---|---|---|---|---|
| 7,275,645 | B2* | 10/2007 | Mallett | A61B 50/10 |
| | | | | 209/702 |
| 7,562,025 | B2* | 7/2009 | Mallett | B07C 7/005 |
| | | | | 705/308 |
| 2005/0065640 | A1* | 3/2005 | Mallett | G06Q 30/018 |
| | | | | 700/224 |
| 2008/0195247 | A1* | 8/2008 | Mallett | G16H 40/67 |
| | | | | 700/225 |
| 2012/0158607 | A1* | 6/2012 | Burns | G06Q 10/0833 |
| | | | | 705/333 |
| 2016/0300297 | A1* | 10/2016 | Kekalainen | G06Q 10/08 |

* cited by examiner

SYSTEM AND METHOD FOR MANAGING MEDICAL WASTE RECEIVED IN ONE OR MORE CONTAINERS

TECHNICAL FIELD

The present disclosure generally relates to waste management systems and more particularly to a system and method for managing medical waste received in one or more containers located at one or more medical facilities.

BACKGROUND

The waste management industry has multiple facets and categories of wastes that are removed from various premises. The hospitals and the medical facilities waste industry is strictly regulated by Environmental Protection Agency (EPA) and Food and Drug Administration (FDA) to ensure that the risk of diseases are kept away from humans, pets, other animals and hence, the environment. A few of the categories of wastes that are hauled from a hospital are regulated medical waste (RMW), sharps, solid waste, recyclable waste and pharmacy (pharma) waste.

Typically, tons of medical wastes are generated in each hospitals and other medical facilities, and more than 50% of such wastes are hazardous to the environment directly or indirectly. The hazardous, for example sharps, and toxic wastes generally have the potential to cause or significantly contribute to an increase in mortality or an increase in serious reversible or irreversible illness. Specifically, sharps including sharp needles, syringes or lancets, etc. pose a substantial hazard to human health when mishandled or improperly collected, stored, transported, disposed of, or otherwise managed. Hence, such hazardous wastes cannot be handled by an individual or by the medical facility, however, requires professionals for collecting, transporting and disposing the same.

Generally, containers are provided for disposing such hazardous wastes, such as sharps, in all the hospitals and other medical facilities, and such wastes need to be timely collected from the hospitals and other medical facilities. Typically, the hospitals or the medical facility call pickup services once the containers are full for collecting the hazardous wastes. However, such method is inefficient as there might be delay in collection and a person has to keep track of the fill level of the containers to inform the pickup services well before the containers are completely full. In addition, if a container gets overfull and spills, it can cause injury to hospital personnel and patients and an inherent liability. Hence, a simple, reliable and scalable technological solution to implement compliance and yet to prevent spillage of hazardous wastes in the hospitals and other medical facilities has been absent for the medical waste industry.

SUMMARY OF THE DISCLOSURE

Thus, there exists a need for a system and method which mitigates some of the disadvantages of the state of the art.

This summary is provided to introduce a selection of concepts in a simple manner that are further described in the detailed description of the disclosure. This summary is not intended to identify key or essential inventive concepts of the subject matter nor is it intended for determining the scope of the disclosure.

A system for managing medical waste received in one or more containers placed at one or more medical facilities is disclosed. In some embodiments, the system comprises one or more tracking modules coupled to the one or more containers, wherein each tracking module comprises, a plurality of LEDs positioned opposite to a plurality of light sensors, wherein each of the LED is being configured to periodically project a light beam towards a light sensor among plurality of light sensors for detecting a fill level of the container, and a controller in communication with the plurality of LEDs and the plurality of light sensors, wherein the controller is being configured for, periodically triggering the plurality of LEDs for projecting the light beams, receiving output data of the plurality of light sensors, the output data representing the fill level of the container, and communicating the fill level of the container to a server. Further, the server in communication with the one or more tracking modules, wherein the server is configured for, determining a pickup schedule for the one or more containers based on the fill level of the one or more containers, wherein the pickup schedule comprises a pickup date and time, and an optimal route for the pickup of the one or more containers, and communicating the pickup schedule to at least one of a pickup service facility or the one or more medical facilities or both. This can be done ahead of time or in real time through communication on the phone as the pick-up service drivers coordinate with the hospitals.

BRIEF DESCRIPTION OF THE FIGURES

The disclosure will be described and explained with additional specificity and detail with the accompanying figures in which.

Figure 1:
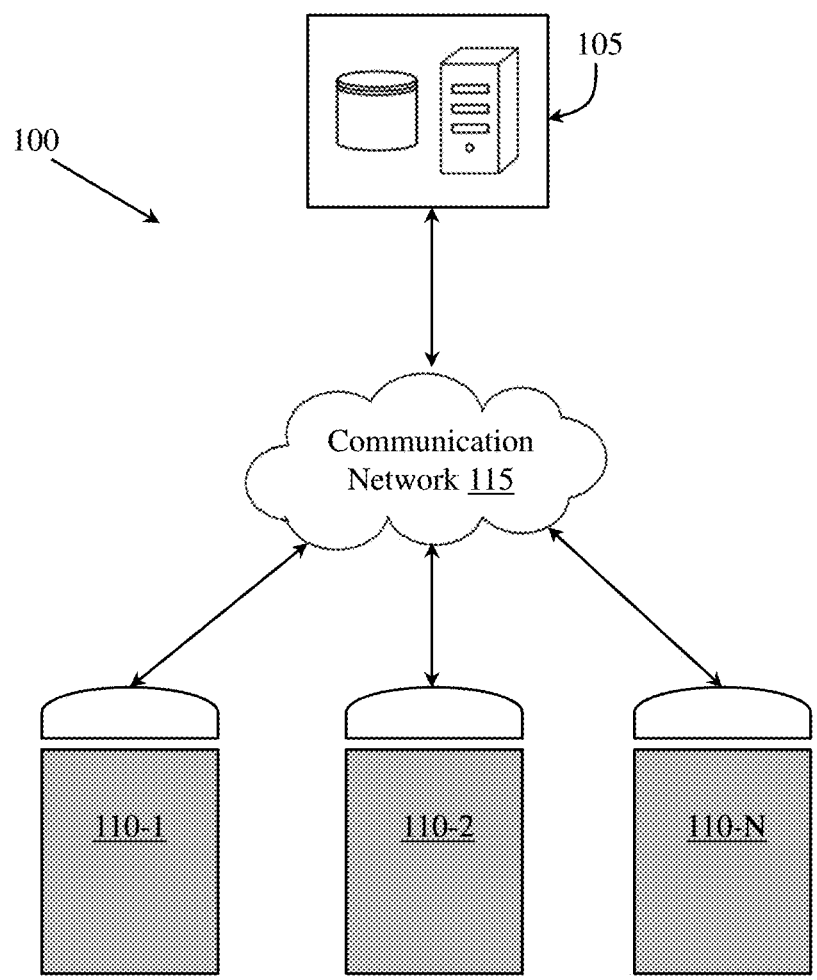
FIG. 1 illustrates an exemplary representation of a system for managing medical waste in which various embodiments of the present disclosure may be seen.

Further, persons skilled in the art to which this disclosure belongs will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those of ordinary skill in the art having benefit of the description herein.

DETAILED DESCRIPTION OF THE EXEMPLARY EMBODIMENTS

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications to the disclosure, and such further applications of the principles of the disclosure as described herein being contemplated as would normally occur to one skilled in the art to which the disclosure relates are deemed to be a part of this disclosure.

It will be understood by those skilled in the art that the foregoing general description and the following detailed description are exemplary and explanatory of the disclosure and are not intended to be restrictive thereof.

The terms "comprises", "comprising", or any other variations thereof, are intended to cover a non-exclusive inclusion, such that a process or method that comprises a list of steps does not include only those steps but may include other steps not expressly listed or inherent to such a process or a method. Similarly, one or more devices or sub-systems or elements or structures or components preceded by "comprises . . . a" does not, without more constraints, preclude the existence of other devices, other sub-systems, other elements, other structures, other components, additional devices, additional sub-systems, additional elements, additional structures, or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this disclosure belongs. The system, methods, and examples provided herein are illustrative only and not intended to be limiting.

Embodiments of the present disclosure will be described below in detail with reference to the accompanying figures.

The embodiments herein disclose a system for managing medical waste received in one or more containers placed at one or more medical facilities, wherein the system comprises a server in communication with one or more containers, placed at the one or more medical facilities, in which medical waste may be disposed. In one embodiment, each container comprises a tracking module for detecting a fill level of the container periodically, and the fill level is then communicated to the server. In another embodiment, upon receiving the fill levels from the one or more containers, the server generates a pickup schedule for the one or more containers based on the fill level of the one or more containers, wherein the pickup schedule comprises a pickup date and time, and an optimal route for the pickup of the one or more containers. Then the server communicates the pickup schedule to one or more pickup service facility or to the pre-defined users. The pickup action can also be triggered in real time by communicating information from the server to a driver enroute to a medical facility. The one or more medical facilities as described herein may include hospitals, clinics, outpatient care centres, specialized care centres, pharmacies, pharmaceutical storage and distribution centres, for example.

FIG. 1 illustrates an exemplary representation of a system for managing medical waste in which various embodiments of the present disclosure may be seen. As shown, the system comprises a server 105 and one or more containers 110-1 to 110-N placed at one or more medical facilities, wherein the server 105 and the one or more containers are communicatively connected via a communication network 115.

The server 105 may include, for example, a computer server or a network of computers or a virtual server which provides functionalities or services for other programs or devices. In one implementation, the server 105 is a cloud server comprising one or more processors, associated processing modules, interfaces and storage devices communicatively interconnected to one another through one or more communication means for communicating information. The storage devices within the server 105 may include volatile and non-volatile memory devices for storing information and instructions to be executed by the one or more processors and for storing temporary variables or other intermediate information during processing. In one embodiment of the present disclosure, the server 105 comprises a database, the database storing information pertaining to the one or more containers (110-1 to 110-N), wherein the information may include container ID, location of each of the container, fill levels, end user details, storage capacity of each of the container, etc.

The communication network 115 may be a wireless network or a wired network or a combination thereof. Wireless network may include long range wireless radio, wireless personal area network (WPAN), wireless local area network (WLAN), mobile data communications such as 3G, 4G, 5G or any other similar technologies. The communication network 115 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like. Further the communication network 115 may include a variety of network devices, including routers, bridges, servers, modems, computing devices, storage devices, and the like. In one implementation, the communication network 115 is the internet which enables communication between the one or more containers 110-1 to 110-N placed at various locations and the server 105.

The one or more containers 110-1 to 110-N may be of any size and shape suitable for storing medical wastes, example sharps, regulated medical waste or pharmacy wastes. Further, said containers may be made of any suitable material, such as polyvinyl chloride, that are sufficiently thick and strong to resist puncture by sharps, for example, syringes, needles and lancets, and the like. Furthermore, the one or more containers 110-1 to 110-N may have wall mounting system, a roll-away cage, a container enclosure for safety, etc.

Figure 2:
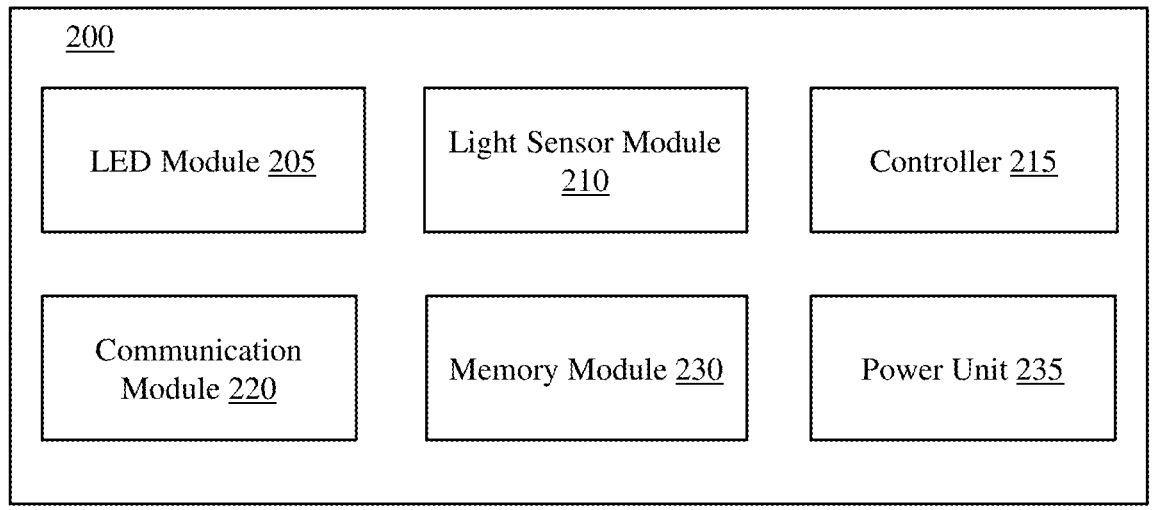
FIG. 2 is a block diagram of an exemplary tracking module in accordance with an embodiment of the present disclosure.

As described, each container comprises a tracking module configured for identifying the fill level of the container. FIG. 2 is a block diagram of an exemplary tracking module in accordance with an embodiment of the present disclosure. As shown, the tracking module 200 comprises a LED module 205, a light sensor module 210, a controller 215, a communication module 220, a memory module 225 and a power supply unit 230. The communication module 220 enables communication between the container and the server 105 through the communication network 115. In one implementation, the communication module 220 comprises means for communicating using mobile data communications such as 3G, 4G, 5G or any other similar technologies. In another implementation, data may be communicated through a local network using any Wi-Fi. The power unit 235 comprises one or more rechargeable or non-rechargeable batteries, voltage regulators and other necessary components for supplying necessary power to the various components of the tracking module 200. Further, the memory module 230 within the tracking module 200 may include volatile and non-volatile memory devices for storing information/data and instructions to be executed by the one or more processors (controller), and for storing temporary variables or other intermediate information during processing.

Figure 3:
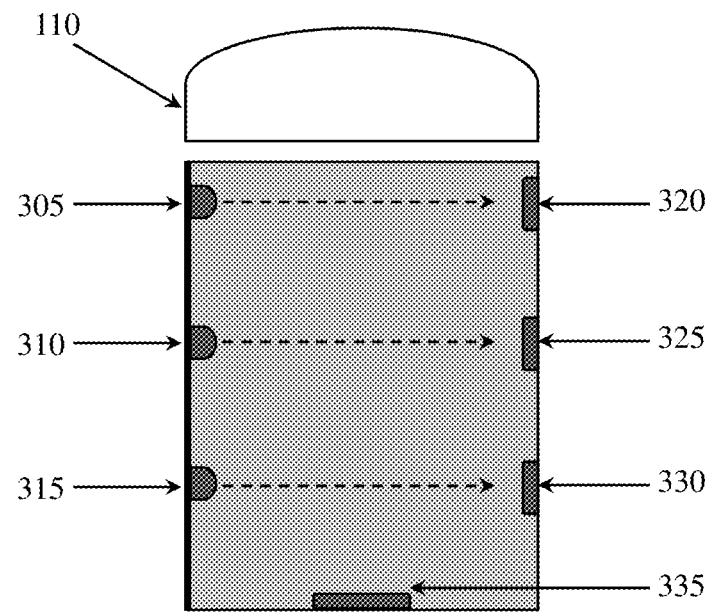
FIG. 3 illustrates an exemplary arrangement of LED module 205 and the light sensor module 210 in an exemplary container 110 in accordance with an embodiment of the present disclosure.

In one embodiment of the present disclosure, the LED module 205 comprises one or more LEDs powered by the power unit 235 through controller 215. Similarly, the light sensor module 210 comprises one or more light sensors, and the output of each light sensor is connected to the controller 215. FIG. 3 illustrates an exemplary arrangement of LED module 205 and the light sensor module 210 in an exemplary container 110 in accordance with an embodiment of the present disclosure. As shown, the LED module comprises three LED sets 305, 310 and 315, and light sensor module comprises three light sensors 320, 325 and 330 placed opposite to the LED sets 305, 310 and 315 respectively so as to receive light emitted from the LEDs 305, 310 and 315. It is to be noted that the LED sets may comprise of single or multitude of LEDs to increase the total lumens and the accuracy of the readings. The LEDs and the light sensors are placed so as to identify various fill levels of the container. In this example, the LED 315 is placed to indicate when the container is 30% full, the LED 310 is placed to indicate when the container is 60% full, and the LED 305 is placed to indicate when the container is 90% full. However, more LED sets and light sensor pairs may be placed for containers of different sizes or for determining various fill levels of the container 110. In one embodiment of the present disclosure, the container 110 comprises a weight sensor 335 for measuring the weight of the container 110. In one implementation, the weight sensor 335 is triggered periodically using the controller 215 and the measured weight data is communicated to the server 105 for further analysis.

Referring back to FIG. 2, the LED module 205 (i.e., the one or more LED sets/groups) and the light sensor module 210 (i.e., the one or more light sensors) are connected to the power unit 235 through the controller 215 for being energized through the controller 215. In one implementation, the LED module 205 and the light sensor module 210 are energised periodically, for example two times in a day, for detecting the fill level of the container 110, hence saving the battery power. Such implementation, which takes advantage of asynchronous clocking and timer circuitry also ensures that malfunctioning due to cyber-attacks, hacking etc. are prevented. Alternatively, the LED module 205 and the light sensor module 210 may be energised continuously for detecting the fill level of the container in real-time or near-real-time. The manner in which the tracking module functions in order to detect various fill levels of the container 100 is described in detail further below, referring to FIG. 2 and FIG. 3.

Referring to FIG. 2 and FIG. 3, when the container 110 is empty, and the LED module 205 and the light sensor module 210 are energised, all the LED groups 305, 310 and 315 emits light beams (in infrared or visible frequency range), and the emitted light beams incident on the light sensors 320, 325 and 330 respectively as shown by the dotted line in FIG. 3. Then the each light sensor 320, 325 and 330 converts the light energy into electrical signals and produces an output pulse representing a logic "0" indicating the controller 215 that the container is empty. In this example, the output of all the three light sensors represents logic "0", and the controller 215 determines that the container 110 is empty.

If the container 110 is half full, and the LED module 205 and the light sensor module 210 are energised, all the LEDs 305, 310 and 315 emits light beams in an infrared or visible frequency range, and the light beams emitted by the LEDs 305 and 310 will incident on the light sensors 320 and 325 respectively. However, the light beam emitted by the LED 315 is interrupted permanently as a result of waste/sharps accumulating in the container 110. Hence the light sensor 330 produces an output pulse, for example, representing logic "1" indicating the controller 215 that the container is half full. Similarly, when the container 110 is full, all the light beams are interrupted by the sharps, and all the light sensors 320, 325 and 330 produces an output pulse representing logic "1" indicating the controller 215 that the container 110 is full. Various other implementations for the said logic are possible. On receiving the fill level, the controller 215 communicates the fill level to the server 105 along with the metadata such as container ID, location, timestamp, weight, etc. In one embodiment of the present disclosure, the controller 215 is configured to monitor the logic state of each of the light sensor's output for a pre-defined time period in order to ensure that the light beam is permanently interrupted as a result of sharps accumulating in the container 110 or in other words, to eliminate false reading by the controller 110. For example, if the LED module 205 and the light sensor module 210 are energised continuously for detecting the fill level of the container in real-time, and when the user drops a sharp, the sharp may interrupt the light beam for an instance and this may communicate a false reading. Hence, in order to avoid such a scenario, the controller 215 checks the output logic state of each of the light sensors for a pre-defined time period to eliminate any false reading.

In one embodiment of the present disclosure, one pair of LED group and light sensor (preferable placed at the top portion of the container) may be used for counting the number of sharps dropped in the container. In such an implementation, a counter (implemented on controller 215) increments a count by "one" whenever the light beam is interrupted by the sharp, and when the light beam is permanently interrupted, i.e., when the output state is "1" for a pre-defined time period, the controller 215 communicates a fill status as "100%" along with the metadata such as container ID, weight, number of sharps accumulated in the container, etc.

Hence, the container comprising the tracking module communicates various fill levels of the container to the server 105 along with the metadata. Such containers may be used in various medical facilities for accumulating the hazardous medical wastes, for example, sharps. In one embodiment of the present disclosure, on receiving various fill levels of the one or more containers, the server 105 determines a pickup schedule for the one or more containers based on the fill level of the one or more containers, wherein the pickup schedule comprises a pickup date and time, and an optimal route for the pickup of the one or more containers. Then the server 105 communicates the pickup schedule to at least one of a pickup service facility or the one or more medical facilities or both. Various scenarios in which the server 105 initiates a pickup event are described in detail further below.

If one or more containers in a given geographical area are completely (100%) full, then the server 105 determines an optimal path for picking up all the containers and generates a pickup schedule, wherein the schedule comprises container IDs, location, pickup date and time, priority, optimal path, information pertaining to the containers such as size, weight, etc. Once the pickup schedule is generated, the server 105 communicates the same or sends a notification to a pickup service facility. An employee of the pickup service may fetch the pickup schedule from the server 105 using a webpage or a dedicated mobile application.

In one embodiment of the present disclosure, the server 105 is configured for generating a pickup schedule based on fill levels of the one or more containers. For example, considering "8" containers that are 100% full and "2"

containers that are 80% full in a given geographical location, then the server 105 generates a pickup schedule including all the "10" containers in order to optimize the process.

In another embodiment of the present disclosure, the server 105 generates a pickup schedule based on the filling rate of the one or more containers, wherein the filling rate is determined based on the fill levels at two or more time instances over a period of time. As described in the present disclosure, the fill levels of the containers are monitored periodically, for example two times in a day. Based on such data, the server 105 determines filling rate of the one or more containers, and generates a pickup schedule for the one or more containers. For example, considering "20" containers in a given geographical area in which "8" containers are filling at a rate of "20%" a day, and remaining (12) are filling at a rate of "5%" a day, then the server 105 generates a first pickup schedule for the "8" containers and a second pickup schedule for the "12" containers, optimizing the pickup process.

As described, an administrator of the system may manage the one or more containers remotely, view all data in the server, and may monitor the fill levels of the one or more containers remotely using a web interface or a mobile application. For example, the administrator may login as administrator using an administrator login interface of the mobile application. On the other hand, an end user or a service provider may use the web interface or the mobile application for monitoring/viewing fill levels of the one or more containers installed in their location. An example service provider or an end-user in a medical waste collection application is a company that provides maintenance services to specific clients. The service provider will be able to retrieve data of all clients who grant the service provider access to their (the client's) data feeds from solution.

Further, the service provider may use the web or mobile interface to validate a completion status of the maintenance service requests in near real time. For instance, in response to a request from the service provider for a scheduled pickup of one or more containers, the system may enable the end user to monitor the current location, an estimated time of the pickup and the like.

Figure 4A:
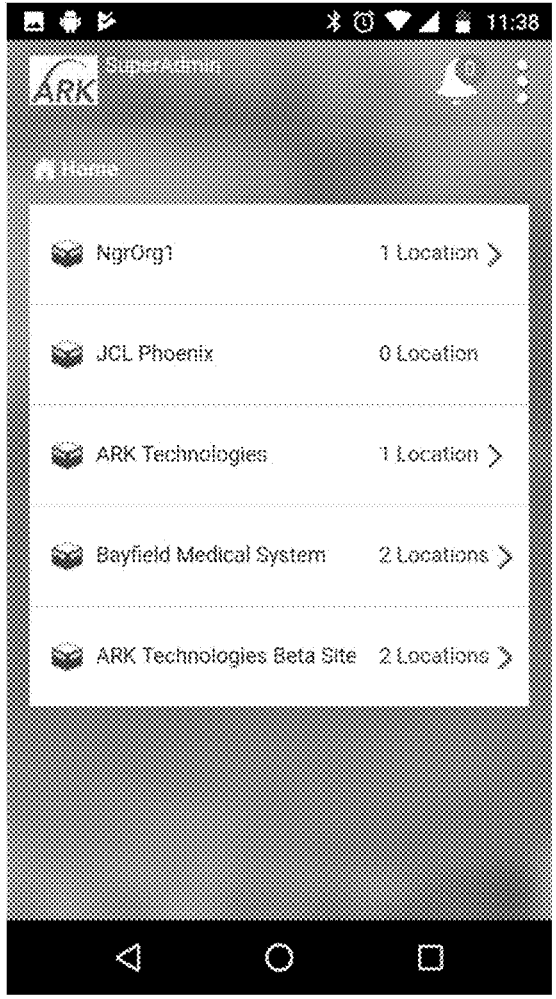
FIGS. 4A, 4B and 4C are exemplary user interfaces of an administrator in accordance with an embodiment of the present disclosure.
Figure 4B:
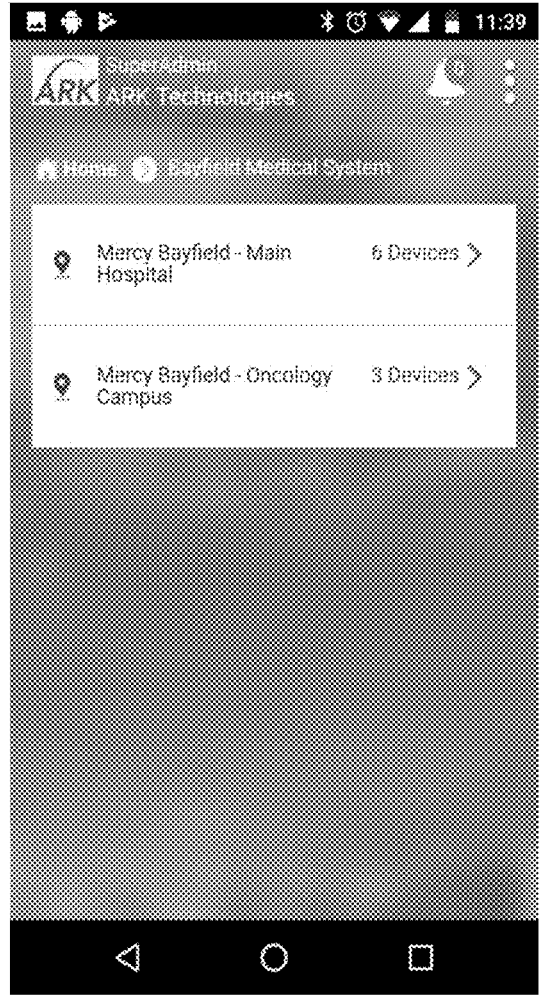
Figure 4C:
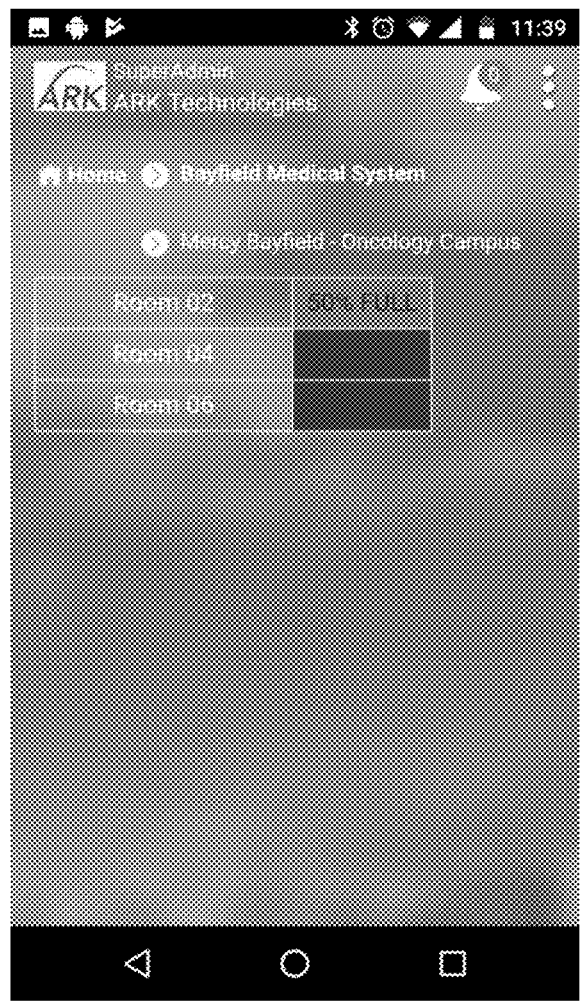

FIGS. 4A, 4B and 4C are exemplary user interfaces of an administrator in accordance with an embodiment of the present disclosure. Once the administrator logs in by providing necessary login credentials (username and password), the application displays one or more clients names along with the location information where the containers are installed as shown in FIG. 4A. In order to view more details, the administrator may select the client name, and upon selecting, the application redirects the administrator to next interface where the administrator may view the locations and number of containers installed in the locations as shown in FIG. 4B. Upon selecting the location, the application displays the information including container name, client address and contact information, installation date, container size, etc. Referring to FIG. 4B, the administrator may click on "devices" to view the status of the one or more containers installed in that particular location. Upon selecting, the application redirects the administrator to a next interface where it displays fill status of the one or more containers installed in that particular location as shown in FIG. 4C. Further it is to be noted that the application is developed to provide a detailed view and complete control over the system for managing one or more clients and associated one or more containers. Further, the administrator may limit or grant access to one or more functions for the one or more clients or service provider based on the requirement.

As can be seen from the foregoing description, the mobile application interface offers an improved and relatively user-friendly method for managing medical waste in accordance with embodiments of the present disclosure. This also enables real-time updates if needed to confirm when a driver in a service provider has made changes. This is particularly valuable in high usage and urgent areas such as emergency rooms (ER).

Further, by implementing the system disclosed in the present disclosure, a pickup service facility may remotely monitor various fill levels of the one or more containers located at various medical facilities. Further, an administrator may remotely set the time for monitoring the fill levels of the container. That is, the solution enables service providers and the end users to alter the way medical waste sensing and collection is managed by automating container inspection and reporting features thereby eliminating the need for manual and/or visual container inspections to assess the fill levels of the waste within one or more containers. Elimination of manual and/or visual inspection requirements reduces the risk of inspection personnel to accidental contact with hazardous waste and exposure to disease or infection. Further, automation of the inspection process also enables targeted container collection through the use automatic alerting of container waste levels through combined use of database, rules engine, web UI, and/or application or mobile app which eliminates numerous person-hours of work and reduces service providers' and end users' exposure to regulatory violations.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

We claim:

1. A system for managing medical waste received in one or more containers placed at one or more medical facilities, the system comprising:
  one or more tracking modules coupled to the one or more containers, each tracking module comprising:
    a plurality of LEDs positioned opposite to a plurality of light sensors, wherein each of the LED is configured for periodically projecting a light beam towards a light sensor among a plurality of light sensors for detecting a fill level of the container;
    a controller in communication with the plurality of LEDs and the plurality of light sensors, wherein the controller is configured for:
      periodically triggering the plurality of LEDs for projecting the light beams;
      receiving output data of the plurality of light sensors, the output data representing the fill level of the container; and communicating the fill level of the container to a server; and an asynchronous network independent, clock timer circuitry for periodically triggering the controller for preventing a cyber-attack and enhancing battery life;

the server in communication with the one or more tracking modules, wherein the server is configured for:

determining a pickup schedule for the one or more containers based on the fill level of the one or more containers, wherein the pickup schedule comprises a pickup date and time, and an optimal route for the pickup of the one or more containers; and communicating the pickup schedule to at least one of a pickup service facility or the one or more medical facilities or both.

2. The system as claimed in claim 1, wherein the each tracking module is uniquely identified using a unique identifier.

3. The system as claimed in claim 1, wherein a plurality of LEDs and the plurality of light sensors are arranged so as to detect various fill levels of the container.

4. The system as claimed in claim 1, wherein the each tracking module further comprises a weight sensor for weighing the containers.

5. The system as claimed in claim 1, wherein determining the pickup schedule for the one or more containers based on the fill level of the one or more containers comprises:

determining filling rate of the each of the one or more containers based on the fill level of the each of the one or more containers; and predicting the pickup schedule for the one or more containers based on the determined filling rate.

6. The system as claimed in claim 1, wherein the server is configured for receiving data from the plurality of tracking modules stationed at plurality of locations for remotely managing medical waste at more than one medical facilities.

7. A method for managing medical waste received in one or more containers placed at one or more medical facilities, the method comprising:

periodically triggering a controller through a network independent, random, and asynchronous clock timer circuitry;

periodically triggering, by the controller, a plurality of LEDs for projecting light beams towards a plurality of light sensors;

receiving, by the controller, output data of the plurality of light sensors, the output data representing the fill level of the container;

communicating, by the controller, the fill level of the container to a server;

determining, by the server, a pickup schedule for the one or more containers based on the fill level of the one or more containers, wherein the pickup schedule comprises a pickup date and time, and an optimal route for the pickup of the one or more containers; and communicating, by the server, the pickup schedule to at least one of a pickup service facility or the one or more medical facilities or both.

8. The method as claimed in claim 7, wherein the periodic triggering of the tracking modules eliminates security threats.

9. The method as claimed in claim 7, further comprising the steps of receiving a request to validate the completion of scheduled pickup, processing the request and returning the results of the request to the end user in near real time.

* * * * *